United States Patent
Imamura

(10) Patent No.: US 10,123,688 B2
(45) Date of Patent: Nov. 13, 2018

(54) INFORMATION PROCESSING APPARATUS, OPERATION METHOD THEREOF, AND COMPUTER PROGRAM

(71) Applicant: CANON KABUSHIKI KAISHA, Tokyo (JP)

(72) Inventor: Hiroshi Imamura, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 171 days.

(21) Appl. No.: 15/139,117

(22) Filed: Apr. 26, 2016

(65) Prior Publication Data
US 2016/0317017 A1 Nov. 3, 2016

(30) Foreign Application Priority Data
Apr. 30, 2015 (JP) ................ 2015-093538

(51) Int. Cl.
A61B 3/00 (2006.01)
A61B 3/14 (2006.01)
A61B 3/10 (2006.01)
A61B 3/12 (2006.01)

(52) U.S. Cl.
CPC .......... *A61B 3/0025* (2013.01); *A61B 3/1025* (2013.01); *A61B 3/1233* (2013.01); *A61B 3/14* (2013.01)

(58) Field of Classification Search
CPC ....... A61B 3/102; A61B 3/1015; A61B 3/112; A61B 3/113; A61B 3/1035; A61B 3/132; A61B 3/152; A61B 3/0058; A61B 3/0041; A61B 3/1225; A61B 3/18; A61B 5/7275; A61B 3/12; A61B 3/0025; A61B 3/1025; A61B 3/14

USPC ........ 351/200, 205, 206, 209–211, 221, 222, 351/243–243
See application file for complete search history.

(56) References Cited

U.S. PATENT DOCUMENTS 6,341,035 B1 * 1/2002 Miura ................ G02B 21/0044
359/363
2005/0225725 A1 * 10/2005 Warden ................ A61B 3/0075
351/216
2013/0293841 A1 11/2013 Frison et al.

FOREIGN PATENT DOCUMENTS

JP 2001-070247 A 3/2001

OTHER PUBLICATIONS

Sulai, Y., et al., "Visualization of retinal vascular structure and perfusion with a nonconfocal adaptive optics scanning light ophthalmoscope", J. Opt. Soc. Am. A, Mar. 2014, pp. 569-579, vol. 31, No. 3.
Scoles, D., et al., "In Vivo Imaging of Human Cone Photoreceptor Inner Segments", IOVS, Jul. 2014, pp. 4244-4251, vol. 55, No. 7.

* cited by examiner

*Primary Examiner* — Brandi Thomas
(74) *Attorney, Agent, or Firm* — Canon USA Inc., IP Division

(57) ABSTRACT

An information processing apparatus includes: an image acquiring unit configured to acquire a plurality of types of images of an eye, including a confocal image and a non-confocal image of the eye; a deciding unit configured to decide a saving format for saving the confocal image and non-confocal image in a storage region; and a saving unit configured to save at least one of the acquired plurality of types of images in the storage region, based on the decided saving format.

17 Claims, 10 Drawing Sheets

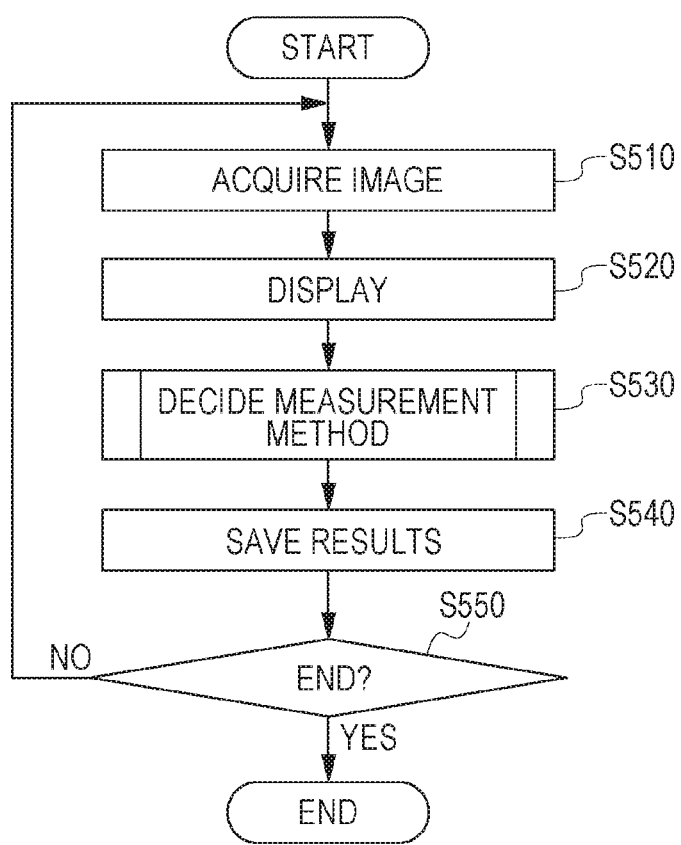

FIG. 6A
FIG. 6B
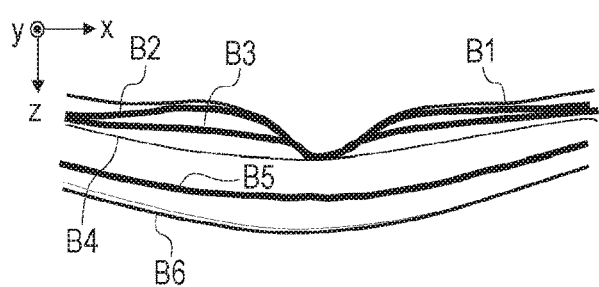
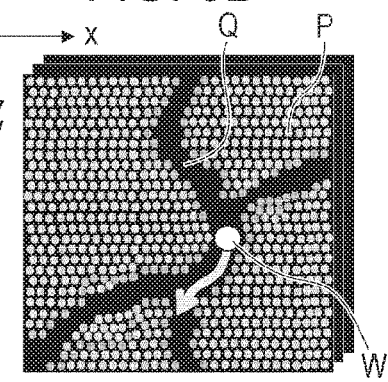
FIG. 6C  FIG. 6D  FIG. 6E  FIG. 6F
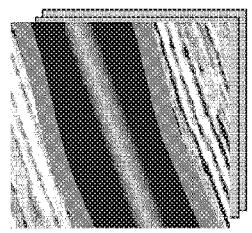
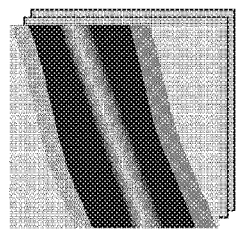
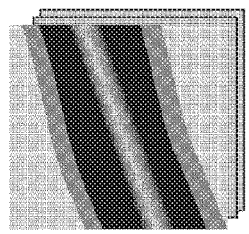
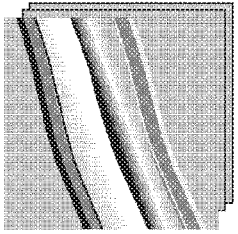
FIG. 6G
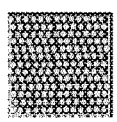
FIG. 6H
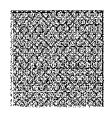
FIG. 6I
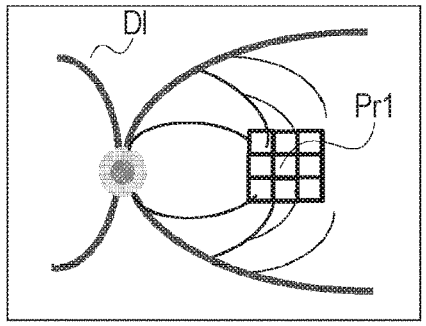
FIG. 6J
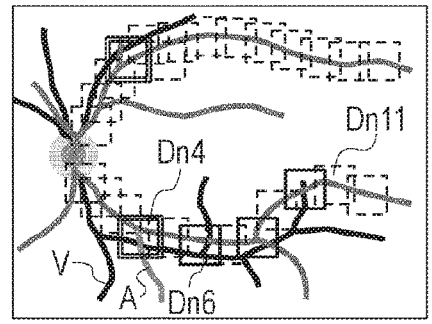
FIG. 6K
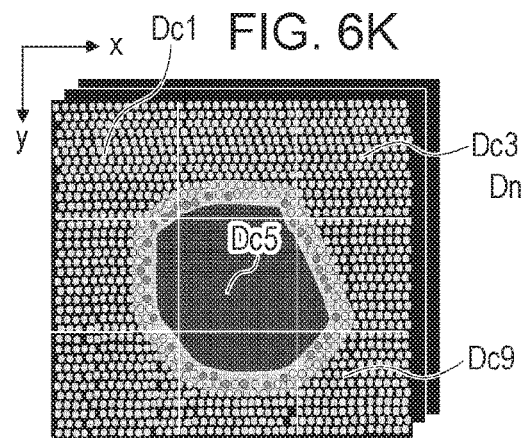
FIG. 6L
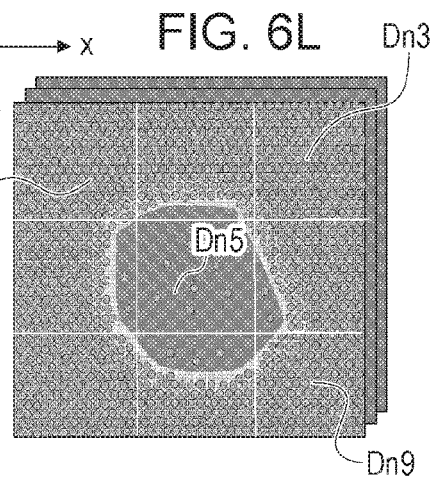

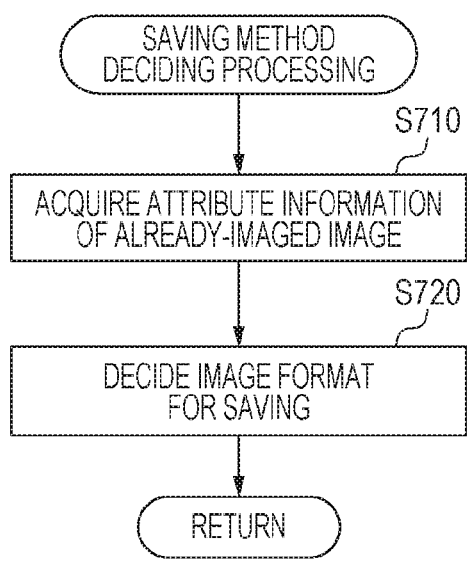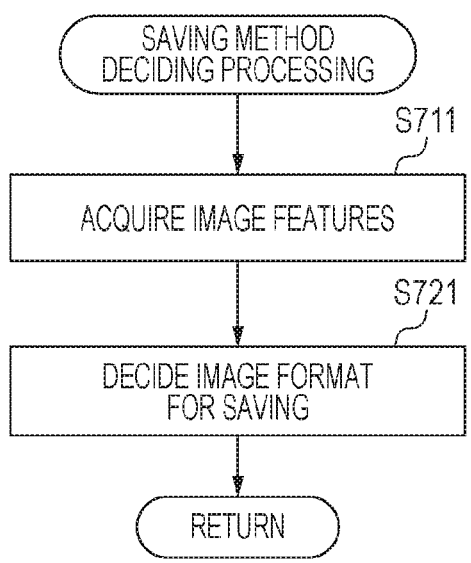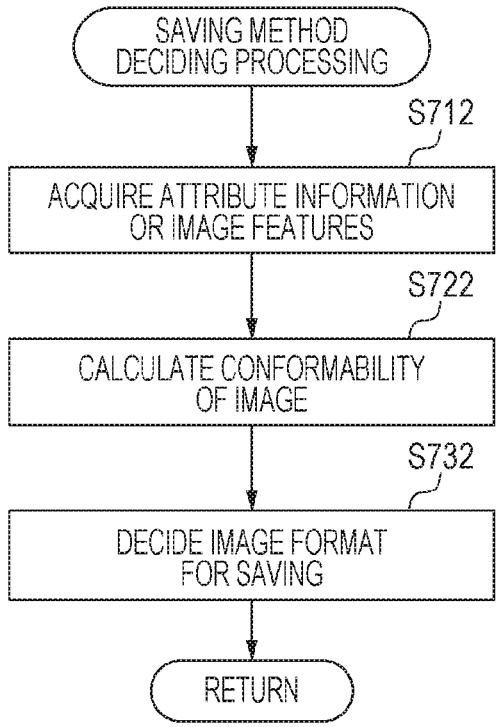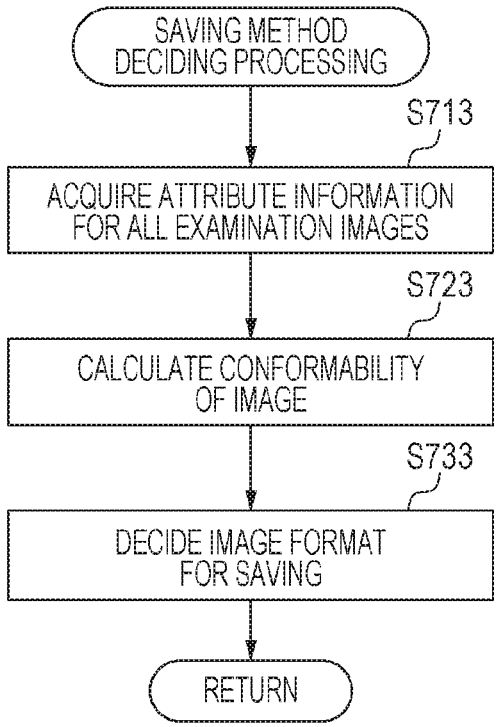

INFORMATION PROCESSING APPARATUS, OPERATION METHOD THEREOF, AND COMPUTER PROGRAM

BACKGROUND OF THE INVENTION

Field of the Invention

The present invention relates to an information processing apparatus used in ophthalmological diagnosis and treatment, an operation method thereof, and a computer program.

Description of the Related Art

Examination of the eye is widely performed for early diagnosis and treatment of lifestyle diseases and diseases which are primary causes of loss of eyesight. The scanning laser ophthalmoscope (SLO), which is an ophthalmological apparatus that employs the principle of confocal laser scanning microscopy, performs high speed raster scanning of a subject's eye with a laser beam, which is measurement light, and acquires a high-resolution planar image of the fundus from the intensity of returning light. Detecting only light that has passed through an aperture (pinhole) enables an image to be formed just using returning light of a particular depth position (focal point), and therefore images with higher contrast than those obtained by fundus cameras and the like can be acquired. An apparatus which obtains such high-contrast planar images will hereinafter be referred to as an SLO apparatus, and a planar image thusly obtained is referred to as an SLO image.

In recent years, increased beam diameter of measurement light in SLO apparatuses has enabled acquisition of SLO images of the retina, with improved horizontal resolution. However, the increased beam diameter of the measurement light has led to deterioration of the S/N ratio and of the resolution of the SLO image during acquisition of SLO images of the retina, due to aberration of the eye being examined. An adaptive optic SLO apparatus has been developed to counter the deterioration of S/N ratio and improve resolution of the SLO image. The adaptive optics SLO apparatus has an adaptive optics system which includes a wavefront sensor and a wavefront correction device. The wave front sensor measures in real time wavefront aberrations caused by the eye being examined, and the wavefront correction device corrects the wavefront aberration occurring in the eye with regard to the measurement light and the returning light. This enables the acquisition of SLO images with high resolution in the horizontal or main-scanning direction so that a high-magnification image can be acquired.

Such a high resolution SLO image can be acquired as a moving image. In order to noninvasively observe hemodynamics (dynamics of blood flow), for example, information on retinal blood vessels is extracted from each frame of an SLO image, and the moving speed of blood cells through capillaries and so forth is measured by performing image analysis. Also, in order to evaluate the visual function of an eye, using an SLO image, photoreceptors P are detected, and the density distribution and array arrangement of the photoreceptors P are calculated.

However, confocal images taken of the inner layers of the retina have intense noise signals due to the influence of light reflecting from the nerve fiber layer, and there have been cases where observing blood vessel walls and detection of wall boundaries has been difficult. Accordingly, as of recent, techniques have come into use using observation of non-confocal images obtained by acquiring scattered light, by changing the diameter, shape, and position of a pinhole on the near side of the light receiving portion. This is described in Sulai, Dubra et al.; "Visualization of retinal vascular structure and perfusion with a nonconfocal adaptive optics scanning light ophthalmoscope", J. Opt. Soc. Am. A, Vol. 31, No. 3, pp. 569-579, 2014 (hereinafter "Sulai and Dubra"). Non-confocal images have a great depth of focus, so objects that have unevenness in the depth direction, such as blood vessels can be easily observed, and also noise is reduced since reflected light from the nerve fiber layer is not readily directly received. While observation of photoreceptors at the outer layers of the retina has primarily involved imaging confocal images of the outer segment of photoreceptors, it has been found that the unevenness of the inner segment of photoreceptors can be imaged in non-confocal images. This is described in Scoles, Dubra et al.; "In vivo Imaging of Human Cone Photoreceptor Inner Segment", IOVS, Vol. 55, No. 7, pp. 4244-4251, 2014 (hereinafter "Scoles and Dubra"). Sulai and Dubra disclose technology for acquiring non-confocal images of retinal blood vessels using an adaptive optics SLO apparatus, while Scoles and Dubra disclose technology for acquiring both confocal images and non-confocal images at the same time using an adaptive optics SLO apparatus.

SUMMARY OF THE INVENTION

An information processing apparatus and an operation method thereof according to an embodiment of the present invention includes: an image acquiring unit configured to acquire a plurality of types of images of an eye, including a confocal image and a non-confocal image of the eye; a deciding unit configured to decide a saving format for saving the confocal image and non-confocal image in a storage region; and a saving unit configured to save at least one of the acquired plurality of types of images in the storage region, based on the decided saving format.

An operation method of an information processing apparatus according to an embodiment of the present invention includes: a step of acquiring a plurality of types of images of an eye, including a confocal image and a non-confocal image of the eye; a step of deciding a saving format for saving the confocal image and non-confocal image in a storage region; and a step of saving at least one of the acquired plurality of types of images in the storage region, based on the decided saving format.

Further features of the present invention will become apparent from the following description of exemplary embodiments with reference to the attached drawings.

BRIEF DESCRIPTION OF THE DRAWINGS

FIG. 5 is a flowchart of processing which the information processing apparatus according to the first embodiment executes.

FIGS. 6A through 6L are diagrams illustrating what is performed in information processing according to the first embodiment.

FIGS. 7A through 7D are flowcharts illustrating the details of processing executed in S530 according to the first embodiment.

DESCRIPTION OF THE EMBODIMENTS

SLO apparatuses that acquire confocal images and non-confocal images generally save all images with the same data amount and format. At this time, there is the possibility that the amount of data being saved will be great as compared to the available capacity. Thus, there is the need to efficiently use data in order to efficiently perform examinations, so there is demand to effectively use limited capacity.

It has been found desirable to effectively save multiple types of images of the eye, including non-confocal images of the eye.

Figure 1:
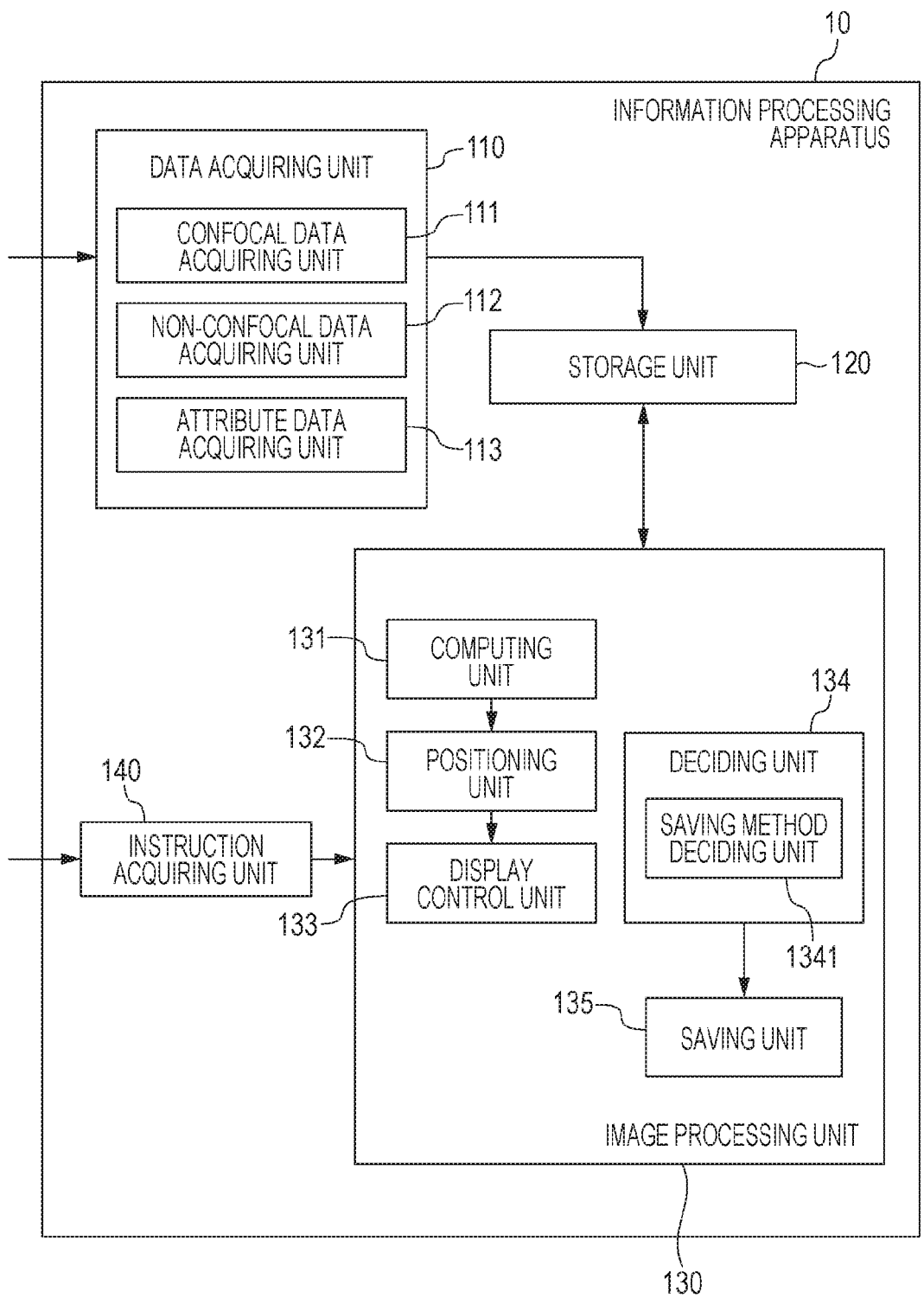
FIG. 1 is a block diagram illustrating a functional configuration example of an information processing apparatus according to a first embodiment.

Accordingly, one aspect of an embodiment includes an image acquiring unit configured to acquire multiple types of images of an eye including at least one type of non-confocal image of the eye (as an example, a data acquiring unit 110 in FIG. 1). One aspect of an embodiment includes a deciding unit configured to decide saving methods that differ for each of multiple types of images that are acquired (as an example, a deciding unit 134 in FIG. 1). One aspect of an embodiment includes a saving unit (as an example, saving unit 135 in FIG. 1) configured to save at least one of the multiple types of images based on the decided saving method. Accordingly, multiple types of images of the eye including at least one type of non-confocal image of the eye can be efficiently saved.

Another aspect of an embodiment includes an image acquiring unit configured to acquire multiple types of images including a confocal image and at least one type of non-confocal image of an eye (as an example, a data acquiring unit 110 in FIG. 1). Another aspect of an embodiment includes a deciding unit configured to decide a saving format to save a confocal image and at least one type of non-confocal image in a storage region (as an example, the deciding unit 134 in FIG. 1). Another aspect of an embodiment includes a saving unit configured to save at least one of multiple types of images that are acquired in a storage region (as an example, the saving unit 135 in FIG. 1). Accordingly, multiple types of images of the eye including a confocal image and at least one type of non-confocal image of the eye can be efficiently saved. Note that the saving format is also referred to as saving method in the present specification.

Another aspect of an embodiment preferably efficiently performs image saving upon having decided the data amount and format, compression method, etc., for saving, in accordance with whether imaged images include anatomical features or disorder portions, and the quality of the imaged images (image quality, and to what degree an imaging planned region is included). That is to say, an apparatus that acquires multiple types of images with different light receiving methods performs image saving with a larger (smaller) data amount with regard to images which are more (less) important with regard to observation and analysis, necessitates technology of saving a great number of images more efficiently. Now, the technology described in Sulai and Dubra discloses technology relating to an adaptive optics SLO apparatus that acquires multi-channel non-confocal images, bud does not disclose a method to efficiently save a great number of types of non-confocal images. Although the technology described in Scoles and Dubra acquires confocal images and non-confocal images at the same time, there is no disclosure of a method of efficiently saving confocal images and non-confocal images.

Embodiments of an image processing apparatus, an operation method thereof, and a computer program, according to the present invention, will be described below with reference to the attached drawings. It should be noted, though, that the present invention is not restricted to this description.

First Embodiment: Deciding Image Saving Method for Each Image Type Beforehand

Figure 3A:
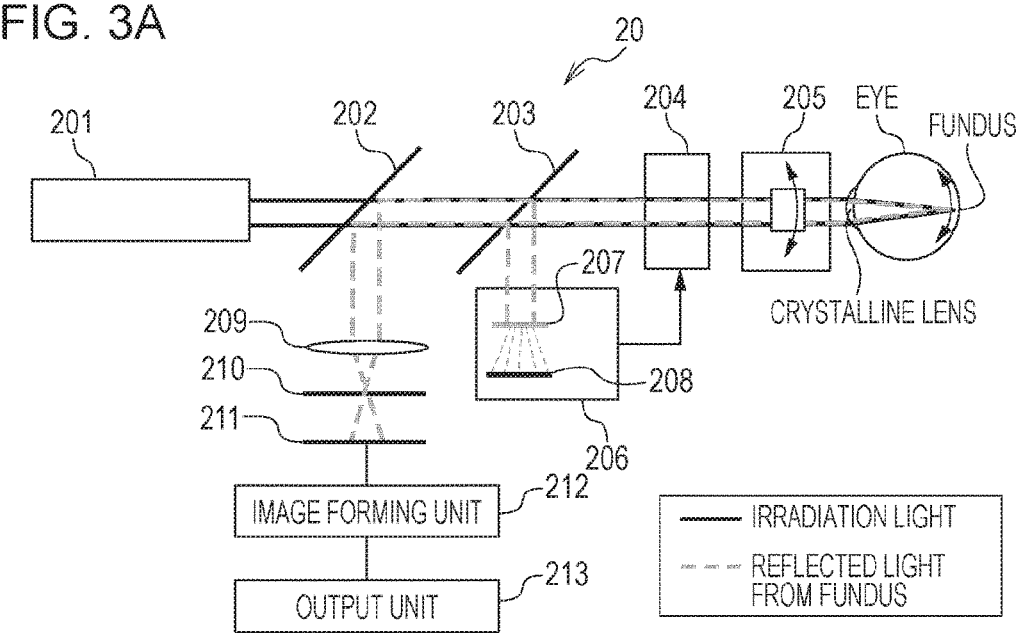
FIGS. 3A through 3H are diagrams for describing the overall configuration of an SLO image imaging apparatus according to the first embodiment.
Figure 3B:
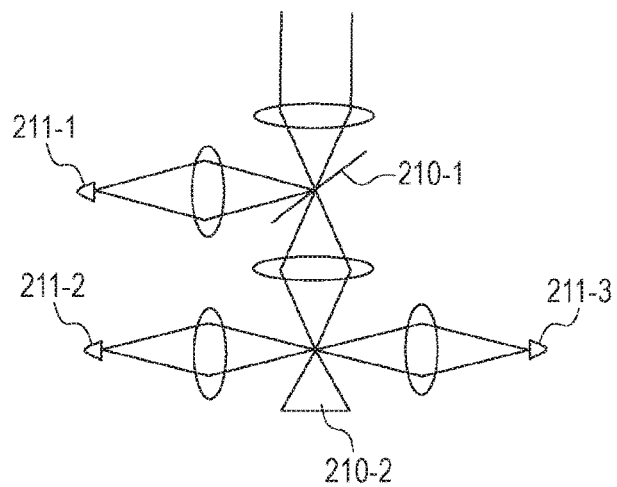

An information processing apparatus according to the present embodiment is configured to uniformly save images by a saving method (saving format) specified for each image type, in a case of imaging photoreceptors of the eye which are an example of an observation object, using an SLO apparatus which is an example of an ophthalmic imaging apparatus that acquires confocal images and non-confocal images at generally the same time. Now, the confocal image and non-confocal image are images taken of the same eye at generally the same timing. Specifically, a confocal image Dc and non-confocal images Dn (Dnr and Dnl) are acquired by an SLO apparatus such as illustrated in FIGS. 3A and 3B that acquires a confocal image Dc and non-confocal images Dn at generally the same timing. A case will be described where moving images and composited images are saved regarding confocal images, while non-confocal images are saved as Split Detector composited images.

Overall Configuration

Figure 2A:
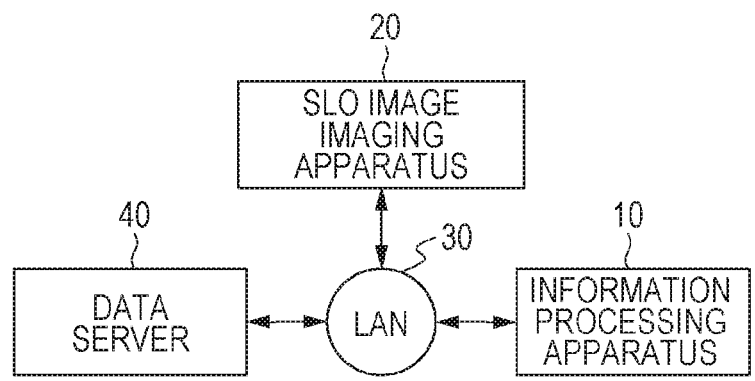
FIGS. 2A and 2B are block diagrams illustrating configuration examples of a system including the information processing apparatus according to the first embodiment.
Figure 2B:
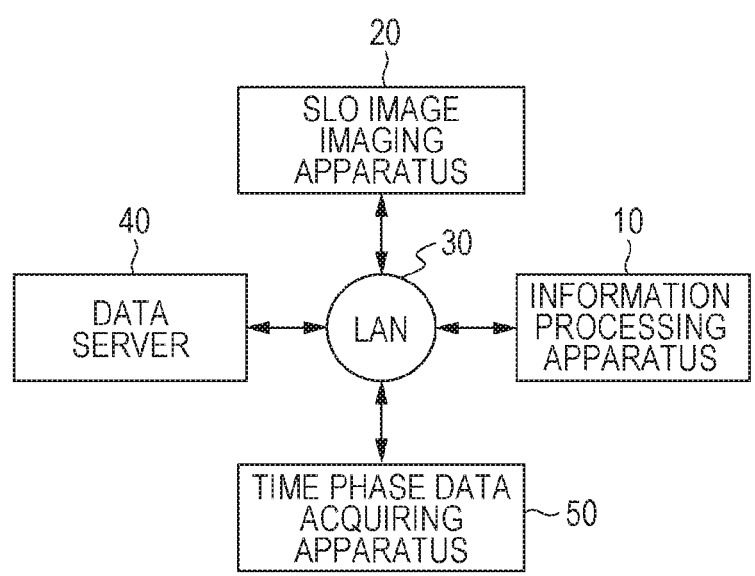

FIGS. 2A and 2B are configuration diagrams of a system including the information processing apparatus 10 according to the present embodiment. The information processing apparatus 10 is communicably connected to an SLO image imaging apparatus 20, which is an example of an ophthalmic imaging apparatus, a data server 40, via a local area network (LAN) 30 including optical fiber, Universal Serial Bus (USB), IEEE 1394, or the like, as illustrated in FIGS. 2A and 2B. The configuration of communicable connection to these devices may be via an external network such as the Internet, or may be a configuration where the information processing apparatus 10 is directly connected to the SLO image imaging apparatus 20. Alternatively, the information processing apparatus 10 may be integrally built into an ophthalmic imaging apparatus.

The SLO image imaging apparatus 20 is an apparatus to image confocal images Dc and non-confocal images Dn, which are wide-angle images Dl and high-magnification images Dh of the eye. The SLO image imaging apparatus 20 transmits wide-angle images Dl, confocal images Dc, non-confocal images Dn, and information of fixation target positions Fl and Fcn used for imaging thereof, to the information processing apparatus 10 and the data server 40. In a case where these images are acquired at different imaging positions, this is expressed as Dli, Dcj, Dnk. That is to say, i and j are variables indicating the numbers for the imaging positions, where i=1, 2, ..., imax, j=1, 2, ..., jmax and k=1, 2, ..., kmax. In a case of acquiring confocal images Dc and non-confocal images Dn at different magnifications, this is expressed like Dc1m, Dc2o, ... (Dn1m, Dn2o, ...) in order from the highest-magnification image, with Dc1m (Dn1m) denoting high-magnification confocal (non-confocal) images, and Dc2o, ... (Dn2o, ...) denoting mid-magnification images.

The data server 40 holds the wide-angle images D1, confocal images Dc, and non-confocal images Dn, of the examinee eye, imaging conditions data such as fixation target positions F1 and Fcn used for the imaging thereof, image features of the eye, and so forth. An external storage apparatus of the data server 40 is an example of a storage region according to the present invention. In the present invention, image features relating to the photoreceptors P, capillaries Q, blood cells W, and retinal blood vessel walls, are handled as image features of the eye. The wide-angle images D1, confocal images Dc, and non-confocal images Dn output from the SLO image imaging apparatus 20, fixation target positions F1 and Fcn used for the imaging thereof, and image features of the eye output from the information processing apparatus 10, are saved in the server 40. Also, the wide-angle images D1, confocal images Dc, and non-confocal images Dn, and image features of the eye, are transmitted to the information processing apparatus 10 in response to requests from the information processing apparatus 10.

FIG. 6B illustrates an example of a high horizontal resolution SLO image. The photoreceptors P, a low-luminance region Q corresponding to the position of capillaries, and a high-luminance region W corresponding to the position of a white blood cell, can be observed. In a case of observing photoreceptors P in the SLO image, the focus position is set nearby the outer layer of the retina (B5 in FIG. 6A) to take a SLO image such as in FIG. 6B. On the other hand, there are retinal blood vessels and capillaries that have branched running through the inner layers of the retina (B2 through B4 in FIG. 6B). Acquiring an adaptive optics SLO image with the focus position set in the inner layers of the retina enables the retinal blood vessel walls to be directly observed.

Next, the functional configuration of the information processing apparatus 10 according to the present embodiment will be described with reference to FIG. 1. FIG. 1 is a block diagram illustrating the functional configuration of the information processing apparatus 10. The information processing apparatus 10 includes a data acquiring unit 110, a storage unit 120, an image processing unit 130, and an instruction acquiring unit 140. The data acquiring unit 110 includes a confocal data acquiring unit 111, a non-confocal data acquiring unit 112, and an attribute data acquiring unit 113. The image processing unit 130 includes a computing unit 131, a positioning unit 132, a display control unit 133, a deciding unit 134, and a saving unit 135. The deciding unit 134 further has a saving method deciding unit 1341.

Now, the SLO imaging apparatus 20 that applies adaptive optics will be described with reference to FIGS. 3A and 3B. The SLO imaging apparatus 20 includes a superluminescent diode (SLD) 201, a Shack-Hartman wavefront sensor 206, an adaptive optics system 204, beam splitters 202 and 203, an X-Y scanning mirror 205, a focus lens 209, a diaphragm 210, a photosensor 211, an image forming unit 212, and an output unit 213.

Light irradiated from the SLD 201 that is the light source is reflected at the fundus. Part of the reflected light is input to the Shack-Hartman wavefront sensor 206 via the second beam splitter 203, and the remaining reflected light is input to the photosensor 211 via the first beam splitter 202. Although the light source here services both as a light source for acquiring confocal images and a light source for acquiring non-confocal images, multiple light sources configured to emit different wavelengths may be used, or the like. The Shack-Hartman wavefront sensor 206 is a device to measure aberration of the eye, in which a lens array 207 is connected to a charge-coupled device (CCD) 208. Upon input light being transmitted through the lens array 207, bright point set appears on the CCD 208, and wave aberration is measured base on the positional gap of the projected bright points. The adaptive optics system 204 drives an aberration correction device (deformable mirror or spatial light phase modulator) to correct the aberration, based on the wave aberration measured by the Shack-Hartman wavefront sensor 206. The light subjected to aberration-correction passes through the focus lens 209 and diaphragm 210, and is received at the photosensor 211. The diaphragm 210 and photosensor 211, respectively, are examples of an aperture and an optical sensor according to the present invention. The aperture preferably is provided upstream of and near to the optical sensor. The scanning position on the fundus can be controlled by moving the X-Y scanning mirror 205, thereby acquiring data according to an imaging region and time (frame rate×frame count) that the operator has instructed. The data is transmitted to the image forming unit 212, where image distortion due to variation in scanning rate is corrected and luminance value correction is performed, thereby forming image data (moving image or still image). The output unit 213 outputs the image data formed by the image forming unit 212. In order to set the focus to a particular depth position on the fundus, at least one of the following can be used; an aberration correction device within the adaptive optics system 204 is adjusted, or an unshown focus adjusting lens is provided within the optical system, and adjustment is performed by moving this lens.

The configuration of the diaphragm 210 and photosensor 211 portion in FIG. 3A is optional, just as long as the SLO imaging apparatus 20 is configured to acquire confocal images Dc and non-confocal images Dn. The present embodiment is configured using a light-shielding member 210-1 (FIGS. 3B and 3E) and photosensor 211-1, 211-2, and 211-3 (FIG. 3B). Regarding the returning light in FIG. 3B, part of the light that has entered the light-shielding member 210-1 disposed at the image forming plate is reflected and enters the photosensor 211-1. Now, the light-shielding member 210-1 will be described with reference to FIG. 3E. The light-shielding member 210-1 is made up of transmitting regions 210-1-2 and 210-1-3, a light-shielded region (omitted from illustration), and a reflecting region 210-1-1, so that the center is positioned on the center of the optical axis of the returning light. The light-shielding member 210-1 has an elliptic shape pattern so that when disposed obliquely as to the optical axis of the returning light, the shape appears to be circular when seen from the optical axis direction. The returning light divided at the light-shielding member 210-1 is input to the photosensor 211-1. The returning light that has passed through the transmitting regions 210-1-2 and 210-1-3 of the light-shielding member 210-1 is split by a prism 210-2 disposed at the image forming plane, and is input to photosensors 211-2 and 211-3, as illustrated in FIG. 3B. Voltage signals obtained at the photosensors are converted into digital values at an AD board within the image forming unit 212, thereby forming a two-dimensional image. The image based on light entering the photosensor 211-1 is a confocal image where focus has been made on a particular narrow range. Images based on light entering the photosensors 211-2 and 211-3 are non-confocal images where focus has been made on a broad range. The light-shielding member 210-1 is an example of an optical member that divides returning light from the eye which has been irradiated by light from the light source, into returning light passing through a confocal region and returning light passing through a non-confocal region. The transmitting regions 210-1-2 and 210-1-3 are examples of a non-confocal region, and non-confocal images are acquired based on the returning light passing through the non-confocal regions. The reflecting region 210-1-1 is an example of a confocal region, and confocal images are acquired based on the returning light passing through the confocal region.

Figures 3C, 3D, 3E, 3F, 3G, 3H:
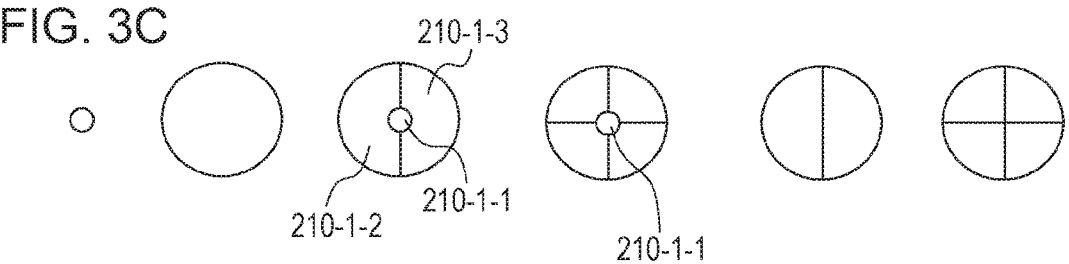

The method for dividing non-confocal signals is not restricted to this, and a configuration may be made where non-confocal signals are divided into four and received, such as illustrated in FIG. 3F, for example. Also, the reception method of confocal signals and non-confocal signals is not restricted to this. For example, a mechanism is preferably had where the diameter and position of the diaphragm 210 (aperture) is changeable. In doing so, at least one of the diameter of the aperture and the position in the optical axis direction is configured so as to be adjustable, so as to receive as confocal signals as illustrated in FIG. 3C and to receive as non-confocal signals as illustrated in FIG. 3D. The diameter and movement amount of the aperture may be optionally adjusted. For example, FIG. 3C shows that the diameter of the aperture can be adjusted to around 1 Airy disc diameter (ADD), and FIG. 3D shows that the diameter of the aperture can be adjusted to around 10 ADD with a movement amount of around 6 ADD. Alternatively, a configuration may be made where multiple non-confocal signals are received at the same time, as in FIGS. 3G and 3H. There are two types of non-confocal signals in the present embodiment, so one will be denoted by Dnr referring to the R channel image, and the other will be denoted by Dnl referring to the L channel image. The notation "non-confocal image Dn" refers to both the R channel image Dnr and L channel image Dnl.

The SLO imaging apparatus 20 can also operate as a normal SLO apparatus, by increasing the scan angle of the scanning optical system in the configuration in FIG. 3A, and instructing so that the adaptive optics system 204 does not perform aberration correction, so as to image wide-angle confocal images and non-confocal images. Images which are lower magnification than the high-magnification images Dc and Dn, and have the lowest magnification of images acquired by the data acquiring unit 110 will be referred to as wide-angle images Dl (Dlc, Dlr, Dll). Accordingly, a wide-angle image Dl may be an SLO image where adaptive optics has been applied, and cases of a simple SLO image are also included. Note that when distinguishing between confocal wide-angle images and non-confocal wide-angle images Dl, these are denoted by Dlc, Dlr, and Dll.

Figure 4:
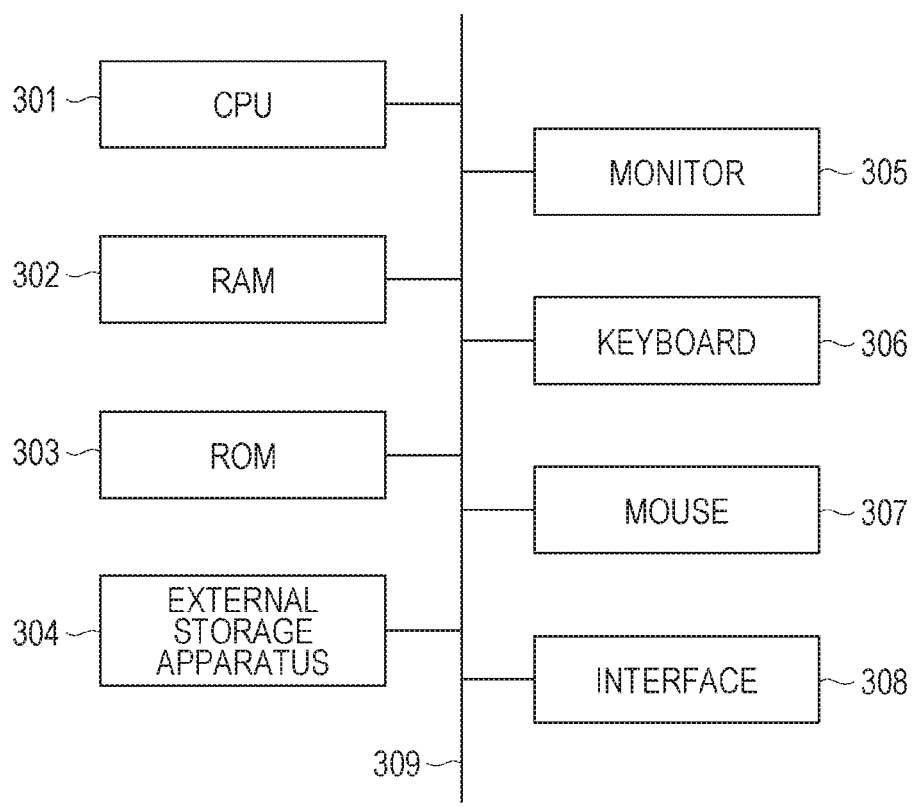
FIG. 4 is a block diagram illustrating a hardware configuration example of a computer which has hardware equivalent to a storage unit and image processing unit and holds other units as software which is executed.

Next, the hardware configuration of the information processing apparatus 10 will be described with reference to FIG. 4. In FIG. 4, 301 denotes a central processing unit (CPU), 302 memory (random access memory (RAM)), 303 control memory (read-only memory (ROM)), 304 an external storage device, 305 a monitor, 306 a keyboard, 307 a mouse, and 308 an interface. The storage device 304 here is an example of the storage region according to the present invention. Control programs for realizing the information processing functions according to the present embodiment, and data used at the time of the control programs being executed, are stored in the external storage device 304. The control programs and data are loaded to the RAM 302 via a bus 309 as appropriate under control of the CPU 301, executed by the CPU 301, and function as the units described below. The functions of the blocks making up the information processing apparatus 10 will be correlated with specific execution procedures of the information processing apparatus 10 illustrated in the flowchart in FIG. 5A.

Step S510: Image Acquisition

The data acquiring unit 110 receives from the SLO image imaging apparatus 20 wide-angle images D1 (Dlc, Dlr, Dll) as illustrated in FIG. 6I, and high-magnification images (confocal images Dcj and non-confocal images Dnrk and Dnlk) at a rectangular region in the macular area, as indicated by Pr1 in FIG. 6I. Acquisition of corresponding fixation target positions F1 and Fcn is also requested. In response to this acquisition request, the SLO imaging apparatus 20 acquires and transmits the wide-angle images Dlc, Dlr, and Dll, confocal images Dcj, and non-confocal images Dnrk and Dnlk, and corresponding fixation target positions Fl and Fcn. The data acquiring unit 110 receives the wide-angle images Dlc, Dlr, and Dll, confocal images Dcj, non-confocal images Dnrk and Dnlk, and fixation target positions Fl and Fcn, from the SLO imaging apparatus 20 via the LAN 30, and stores these in the storage unit 120.

Step S520: Display

The computing unit 131 performs computation between non-confocal data (Dln or Dn) according to the computation instructed via the instruction acquiring unit 140, and additionally generates non-confocal images. Next, the positioning unit 132 performs image positioning, and the display control unit 133 displays the confocal images and non-confocal images. Assumption will be made in the present embodiment that the instructed computation is Split Detector (computation of (pixel value of L-channel image−pixel value of R-channel image)/(pixel value of R-channel image+ pixel value of L-channel image)). The computing unit generates Split Detector images (Dlns and Dns). The computation performed by the computing unit 131 is not restricted to this, and any computation processing may be performed. FIGS. 6G and 6H illustrate examples of a confocal image Dc and Split Detector image Dns in a case of imaging photoreceptors. The positioning unit 132 performs inter-frame positioning of the wide-angle images Dlc and non-confocal image Dc. Specifically, i) The positioning unit 132 sets a reference frame to serve as a reference for positioning. In the present embodiment, the frame with the smallest frame No. is the reference frame. Note that the frame setting method is not restricted to this, and any setting method may be used.

ii) The positioning unit 132 performs general inter-frame correlation (rough positioning). Although any positioning technique may be used, the present embodiment performs rough positioning using a correlation coefficient as an inter-image similarity evaluation function, and Affine transform as a coordinate conversion technique.

iii) The positioning unit 132 performs fine positioning based on the correspondence relation in the general position among the frames.

In the present embodiment, images that have been subjected to the rough positioning obtained in ii) are then subjected to inter-frame fine positioning, using free form deformation (FFD), which is a type of a non-rigid positioning technique. Note that the fine positioning technique is not restricted to this, and any positioning technique may be used. The inter-frame positioning parameter values decided regarding the wide-angle image Dlc and non-confocal image Dc are applied not only to Dlc and Dc but also to each of the wide-angle images Dlr, Dll, and Dlns, and confocal images Dnr, Dnl, and Dns as well, and inter-frame positioning is performed. Further, compositing processing is performed on the moving images Dlc, Dlr, Dll, Dlns, Dc, Dnr, Dnl, and Dns regarding which inter-frame positioning has been completed.

Next, the positioning unit 132 performs positioning of the composited image of wide-angle image Dlc and the composited image of high-magnification image Dcj, and finds the relative position of Dcj on Dlc. The positioning unit 132 acquires the fixation target position Fcn used at the time of imaging the high-magnification non-confocal images Dcj from the storage unit 120, to use as the initial point for searching for positioning parameters for the positioning of the wide-angle image Dlc and confocal image Dcj. The positioning of the wide-angle image Dlc and high-magnification non-confocal image Dcj is performed while changing combinations of the parameter values. The combination of parameter values where the similarity between the composited image of wide-angle image Dlc and composited image of high-magnification confocal image Dcj is highest is decided to be the relative position of the confocal image Dcj as to the wide-angle image Dlc. Note that the positioning technique is not restricted to this, and any positioning technique may be used.

Also, in a case where a mid-magnification image has been acquired in S510, positioning is performed from images with lower magnification. For example, in a case where a high-magnification non-confocal image Dc1m and a mid-magnification non-confocal image Dc2o have been acquired, first, the wide-angle image Dlc and the mid-magnification image Dc2o are positioned, and next, the mid-magnification image Dc2o and the high-magnification confocal image Dc1m are positioned.

Further, image tiling parameter values decided regarding the wide-angle confocal image Dlc and confocal image Dcj are applied to tiling of the non-confocal images Dlr and Dnrk, Dll and Dnlk, Dlns and Dnsk) as well. The relative positions of the high-magnification non-confocal images Dnrk, Dnlk, and Dnsk on the wide-angle non-confocal images Dlr, Dll, and Dlns are each decided.

The display control unit 133 displays the formed image group on the monitor 305. The composited images here are displayed tiled using the positioning parameters described above. Also, composited images or moving images regarding which inter-frame positioning has been completed are displayed using the inter-frame positioning parameter values, at imaged positions instructed via the instruction acquiring unit 140. The type of images to be display is switched using a graphical user interface (GUI) that has been prepared for this purpose. Although radio buttons are used for switching in the present embodiment, any GUI arrangement may be used for the switching. The types of images to be switched are the four of confocal image Dc, R channel image Dnr, L channel image Dnl, and Split Detector images Dns. The display control unit 133 may perform display correcting the concentration among confocal images Dcj and among non-confocal images Dnk, in a case where multiple confocal images Dcj and non-confocal images Dnk have been acquired. Any known luminance correction method may be used. In the present embodiment, the concentration difference is corrected by performing linear transformation of luminance values of each image Dcj and Dnk so that the averages and variances of histograms Hj and Hk, generated at the images Dcj and Dnk, are common between the images Dcj and Dnk. Note that the method of luminance correction among confocal images and non-confocal images is not restricted to this, and any known luminance correction method may be used. Further, an image specified by the operator is enlarged to an instructed display scale and displayed on the monitor 305 via the instruction acquiring unit 140.

Step 530: Deciding Data Saving Method

The saving method deciding unit 1341 acquires attribute information of imaged images from the attribute data acquiring unit 113. Next, the saving method deciding unit 1341 decides saving image formats, data compression methods, filenames, and saving location (path), for the image types to be saved in the data server 40, as instructed by the instruction acquiring unit 140. Confocal images and Split Detector images are instructed to be saved in the present embodiment. Note that saving method deciding unit 1341 does not necessarily have to decide the saving filename and saving location; for example, decision may be made by acquiring filenames and saving location specified by the user via the instruction acquiring unit 140. Detailed saving method deciding processing will be described in detail in S710 to S720.

Step S540: Saving Results

The saving unit 135 transmits to the data server 40 examination date, information identifying examinee eye, fixation target positions F1 and Fcn, and positioning parameter values, correlated with the moving images Dlc and Dc, and Dlns and Dns, based on the saving method for image types to be saved, decided in S530. The data transmitted to the data server 40 is saved at a specified location (path) within an external storage apparatus within the data server 40. The saving location of data (images, etc.) saved by the saving unit 135 is not restricted the external storage apparatus within the data server 40, and may be saved in the data server 40 or an external storage apparatus connected to the external storage apparatus 304. The external storage apparatus may be any of a hard disk drive (HDD), storage device using semiconductors (solid state drive (SSD) or Universal Serial Bus (USB)), a storage apparatus using magnetic tape, and a storage apparatus using an optical disc.

Step S550: Decision of Whether or not to End

The instruction acquiring unit 140 externally acquires an instruction regarding whether or not to end processing of the wide-angle images Dl, high-magnification confocal images Dcj, and high-magnification non-confocal images Dnk, by the information processing apparatus 10. This instruction is input by an operator by way of the keyboard 306 or mouse 307, for example. In a case where an instruction for ending of processing is acquired, the processing ends. On the other hand, in a case of acquiring an instruction to continue processing, the flow returns to S510, and processing on the next examinee eye (or redoing the processing on the same examinee eye) is performed. The processing executed in S520 will be described in detail with reference to the flowchart in FIG. 7A.

Step S710: Acquiring Attribute Information of Imaged Image

The saving method deciding unit 1341 acquires attribute information of imaged images from the attribute data acquiring unit 113. Specifically, attribute information is date of image type (confocal/R channel/L channel/Split Detector image), resolution, number of gradations, and number of frames, of the images.

Step S720: Deciding Image Format for Saving

The saving method deciding unit 1341 decides the image types to be saved, image format for saving, and data compression method. Generally, in cases of observing photoreceptors, confocal images that enable outer segments of photoreceptors to be observed, and Split Detector images that enable inner segments of photoreceptors to be observed, are used. Accordingly, assumption will be made that only confocal images and Split Detector images are specified as image types to be saved. Next, the saving method deciding unit 1341 decides the following items for the image types to be saved.

Number of gradients
Resolution
Number of frames (frame rate)
Image format or image generating method
Data compression method Generally, in a case of observing photoreceptors, confocal images are primarily observed, and regions on Split Detector images corresponding to low-luminance regions on confocal images are supplementally observed. Accordingly, it is efficient to allocate much data to be saved for confocal images and little data for Split Detector images. Accordingly, in the present embodiment, all confocal images are uniformly saved using 16-bit
Same resolution as original image
Same number of frames as original image
Moving image (AVI)
Uncompressed while all Split Detector images are uniformly saved using the following.

16-bit
Same resolution as original image
1
Composited image
Uncompressed

These instructions may be input to the image processing unit 130 via the instruction acquiring unit 140 by the user specifying the image types to save, image formats, and compression methods from a saving menu displayed on the monitor 305 using the keyboard 306 and mouse 307. Alternatively, this may be executed as a preset saving method without user specifications. Although description has been made in the present embodiment that both confocal images and Split Detector images are saved at the same number of gradients, the same resolution, and the same compression method, the present invention is not restricted to this. For example, the confocal images may be decided to be 16-bit images and the Split Detector images to be 8-bit images. Alternatively, composited images of confocal images may be saved as non-compressed data such as a bitmap, while composited images of Split Detector images are saved as JPEG compressed data. Further, the confocal images may be saved as moving images with a frame rate of 32, while the Split Detector images are saved as moving images with a frame rate of 16. Alternatively, the saving resolution of confocal images may be decided to be 400 pixels×400 pixels and the saving resolution of Split Detector images 200 pixels×200 pixels. Note that the saving method deciding unit 1341 specifies predetermined filenames and saving locations in the external storage apparatus (actually a path including computer name, drive name, folder name, and filename) necessary to save data such as images and the like. However, this is not restrictive, and an arrangement may be made where information (path) relating to a filename and saving location specified by the user is acquired via the instruction acquiring unit 140 and decided. According to the above-described configuration, the information processing apparatus 10 uniformly saves images according to a saving method specified for each image type, when imaging photoreceptors using a SLO apparatus that takes confocal images and non-confocal images at the same time. Accordingly, images of the eye that are crucial for observation and analysis can be efficiently saved.

Although the saving format (saving method) for each type of the multiple types of images is decided beforehand with the present embodiment, a configuration may be made where the saving format for each type of the multiple types of images can be changed by user specification (e.g., selecting a saving format). Also, different saving formats are preferably decided for each type of the multiple types of images. For example, a saving format may be decided where confocal images are given priority over non-confocal images, with the non-confocal images not being saved. Conversely, a saving format may be decided where non-confocal images are given priority over confocal images, with the confocal images not being saved. Also a saving format of not saving confocal images may be decided. Also, the saving formats that are decided preferably include a saving format that images are not saved. That is to say, the decision of the saving format preferably includes decision of whether or not to save images. The saving format is preferably decoded in accordance with the object of observation in multiple types of images (e.g., photoreceptors and blood vessels). For example, the saving format is preferably decided so that the relationship in magnitude of the number of frames saved in the storage region for confocal images (example of data amount) and the number of frames saved in the storage region for non-confocal images differs. In a case where the object of observation is photoreceptors at this time, confocal images are more suitable than non-confocal images, so a greater number of frames of confocal images is preferably saved. On the other hand, in a case where the object of observation is blood vessels, non-confocal images are more suitable than confocal images, so fewer frames of confocal images are preferably saved. The above-described embodiment is applicable in the following embodiments as well.

Second Embodiment: Deciding Image Saving Method by Feature Regions in Image

An information processing apparatus according to a second embodiment performs the following processing on images taken with an SLO apparatus that acquires confocal images and non-confocal images at the same time. Instead of uniformly saving according to a saving method specified for each image type as in the first embodiment, the information processing apparatus is configured so that, based on image features or disorder candidate regions, the more crucial a portion for observation or image analysis included in an image is, the more data amount is allocated when saving. Specifically, an SLO apparatus such as illustrated in FIGS. 3A and 3B that acquires confocal images Dcj and non-confocal images Dnk at the same time, acquires confocal images Dcj and non-confocal images Dnk of retinal blood vessels, which is an example of an observation object, at acquisition positions such as illustrated in FIG. 6J. Although a region where an initial disorder has damaged the outer segment but the inner segment has survived, this is imaged as a black defect area in confocal images (Dc5 in FIG. 6K), but can be observed as a region where high-luminance granular objects exist in non-confocal images (Dn5 in FIG. 6L). A case will be described where the more arteriovenous crossing portions, which are areas of predilection for retinal vein occlusion, are included in an image, the more data amount is allocated when saving.

FIG. 2B illustrates the configuration of an apparatus connected to the information processing apparatus 10 according to the present embodiment. The present embodiment differs from the first embodiment in that the information processing apparatus 10 is connected to a time phase data acquisition apparatus 50, in addition to the SLO imaging apparatus 20. The time phase data acquisition apparatus 50 is an apparatus that acquires biosignal data (time phase data) that autonomously and cyclically changes, such as a sphygmograph or electrocardiograph, for example. The time phase data acquisition apparatus 50 acquires time phase data Sj at the same time as acquiring high-magnification images Dnk, in accordance with operations performed by an unshown operator. The acquired time phase data Sj is sent to the information processing apparatus 10 and data server 40. Note that the time phase data acquisition apparatus 50 may be directly connected to the SLO imaging apparatus 20.

In addition to the wide-angle images Dlr and Dll and high-magnification images Dnrk and Dnlk of the examinee eye, and acquisition conditions such as the fixation target positions Fl and Fcn used at the time of acquisition, the data server 40 also holds image features of the eye. Any image features of the eye may be used, but the present embodiment handles retinal blood vessels and capillaries Q, and photoreceptor damage regions. The time phase data Sj output from the time phase data acquisition apparatus 50 and image features output from the information processing apparatus 10 are saved in the server. The time phase data Sj and image features of the eye are transmitted to the information processing apparatus 10 upon request by the information processing apparatus 10.

Figure 8:
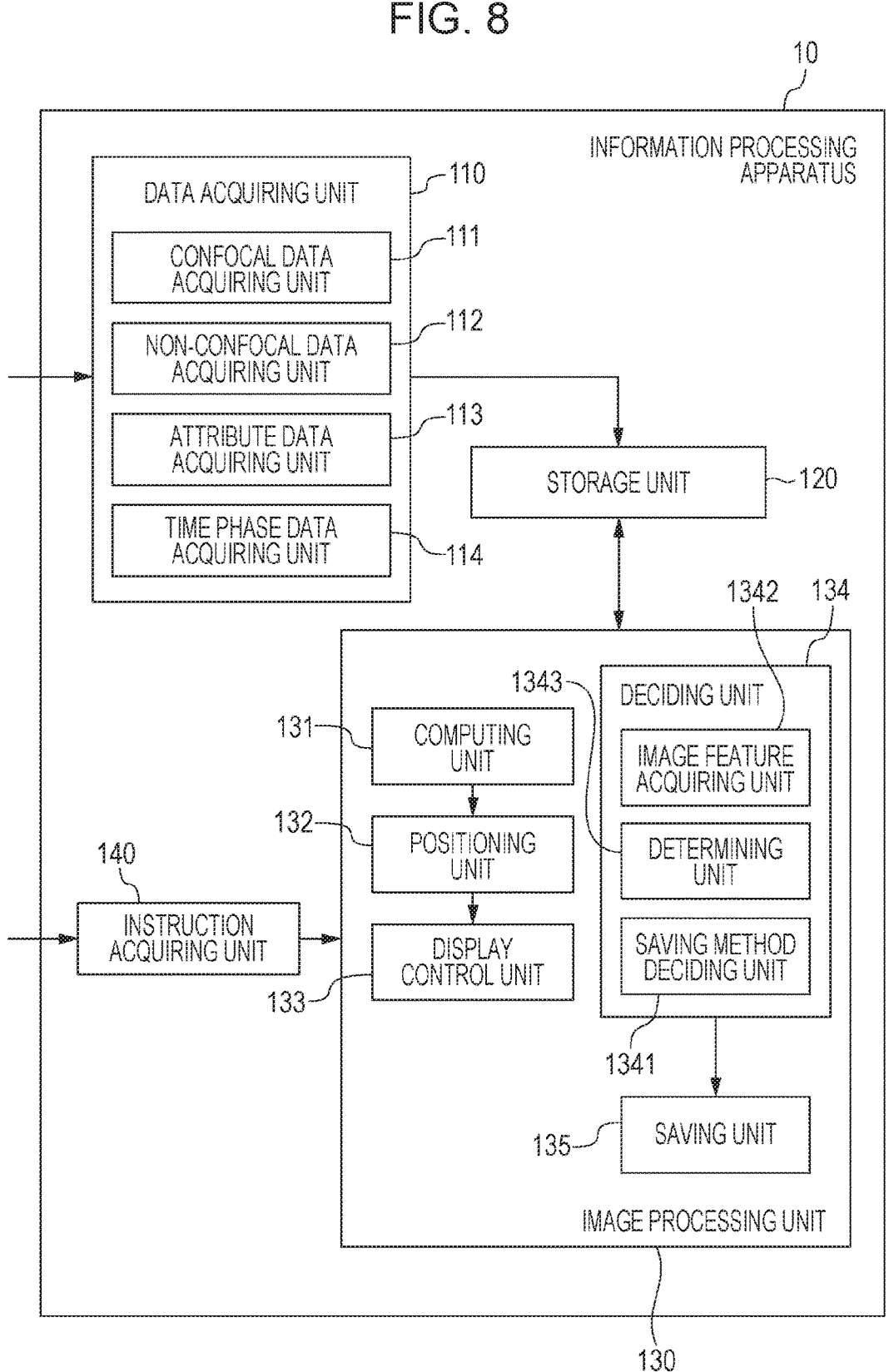
FIG. 8 is a block diagram illustrating a functional configuration example of an information processing apparatus according to a second embodiment.

Next, FIG. 8 illustrates a functional block diagram of the information processing apparatus 10 according to the present embodiment. This configuration differs from the first embodiment with regard to the point that the data acquiring unit 110 has a time phase acquiring unit 114, and the deciding unit 134 has an image feature acquiring unit 1342 and determining unit 1343. The image processing flow according to the present embodiment is the same as that illustrated in FIG. 5. Other than S510, S520, and S530, the flow is the same as in the first embodiment, so just the processing of S510, S520, and S530, will be described in the present embodiment.

Step S510: Image Acquisition

The data acquiring unit 110 acquires wide-angle images Dlc and Dln, confocal images Dcj, non-confocal images Dnk, and time phase data. Confocal images Dcj and non-confocal images Dnk are acquired following a retinal artery arcade A in the present embodiment, as illustrated in FIG. 6J. The time phase acquiring unit 114 requests the time phase data acquisition apparatus 50 for time phase data Sj relating to biological signals. In the present embodiment, a sphygmograph serves as a time phase data acquisition apparatus, used to acquire pulse wave data Sj from the earlobe of the subject. This pulse wave data Sj is expressed with acquisition time on one axis and a cyclic point sequence having the pulse wave signal values measured by the sphygmograph on the other axis. The time phase data acquisition apparatus 50 acquires and transmits the time phase data Sj corresponding to the acquisition request. The time phase acquiring unit 114 receives this pulse wave data Sj from the time phase data acquisition apparatus 50 via the LAN 30. The time phase acquiring unit 114 stores the received time phase data Sj in the storage unit 120.

Now, there are two conceivable timings relating acquisition of the time phase data Sj by the time phase data acquisition apparatus 50; one is a case where the confocal data acquiring unit 111 or image processing method deciding unit 1312 starts image acquisition in conjunction with a particular phase of the time phase data Sj, the other is a case where acquisition of pulse wave data Pi and image acquisition are simultaneously started immediately after an image acquisition request. In the present embodiment, acquisition of pulse wave data Pi and image acquisition are simultaneously started immediately after an image acquisition request. The time phase data Pi of each image is acquired by the time phase acquiring unit 114, the extreme value in each time phase data Pi is detected, and the cardiac cycle and relative cardiac cycle are calculated. The relative cardiac cycle is a relative value represented by a floating-point number between 0 and 1 where the cardiac cycle is 1.

The data acquiring unit 110 requests the SLO imaging apparatus 20 for acquisition of wide-angle images Dlc, Dlr, and Dll, confocal images Dcj, non-confocal images Dnrk and Dnlk, and corresponding fixation target position Fl and Fcn data. In response to the request, the SLO imaging apparatus 20 acquires and transmits the wide-angle images Dlc, Dlr, and Dll, confocal images Dcj, non-confocal images Dnrk and Dnlk, and corresponding fixation target positions Fl and Fcn. The data acquiring unit 110 receives the wide-angle images Dlc, Dlr, and Dll, confocal images Dcj, non-confocal images Dnrk and Dnlk, and corresponding fixation target positions Fl and Fcn, from the SLO imaging apparatus 20 via the LAN 30, and stores these in the storage unit 120. FIGS. 6C and 6D illustrate an example of a confocal image Dc and non-confocal image Dnr in a case of having photographed a retinal blood vessel. The confocal image Dc has strong reflection from the nerve fiber layer, so the background noise makes positioning difficult. The non-confocal image Dnr (Dnl) of the R channel (L channel) has higher contrast at the blood vessel wall at the right side (left side).

On the other hand, examples of non-confocal images are not limited to this. Other examples include an addition process image Dnr+l of non-confocal images Dnr and Dnl, and a Split Detector images Dnsd to which a type of differential processing ((L−R)/(R+L)) has been applied. FIGS. 6E and 6F illustrate examples of Dnr+l and Dnsd. When "Non-confocal image Dnk" is used below, this can be applied to any non-confocal images Dnk, but description will be made that unless stated otherwise, Dnr+l is used.

Step S520: Display

The computing unit 131 performs computation between non-confocal data (Dnl or Dn) according to the computation instructed via the instruction acquiring unit 140, and additionally generates a non-confocal image. Next, the positioning unit 132 performs positioning, and the display control unit 133 displays the confocal images and non-confocal images. Assumption will be made in the present embodiment that the instruction acquiring unit 140 has instructed R+L as the computation, i.e., (pixel values of the R-channel image+pixel values of the L-channel image). The computing unit 131 generates the (R+L) image (Dlnr+l and Dnr+l). The computation performed by the computing unit 131 is not restricted to this, and any computation processing may be performed. The positioning unit 132 performs inter-frame positioning of wide-angle images Dlr+l and non-confocal images Dnr+l and compositing, and further performs tiling of composited images of wide-angle images Dlr+l and composited images of high-magnification images Dnr+lk. Specific procedures of inter-frame positioning processing, compositing processing, and tiling processing are the same as in the case of the first embodiment, so description will be omitted.

Further, the point where the decided inter-frame positioning parameters are applied to image so other image types (wide-angle images Dlc and high-magnification images), and moving images which have been subjected to inter-frame positioning are composited, is no different from the first embodiment. Moreover, the point where the tiling parameter values decided from the wide-angle confocal images Dlr+l and confocal images Dnr+l are also applied to tiling of the non-confocal images Dnrk and (Dlr and Dnrk, Dll and Dnlk, Dlns and Dnsk) is the same as in the first embodiment. The display control unit 133 displays the formed image group on the monitor 305. The composited images here are displayed tiled using the tiling parameters described above. Also, composited images or moving images regarding which inter-frame positioning has been completed are displayed using the inter-frame positioning parameter values, at imaged positions instructed via the instruction acquiring unit 140.

Step S530: Deciding Data Saving Method

The image feature acquiring unit 1342 acquires the retinal blood vessel regions and arteriovenous crossing portions as image features from the wide-angle images Dln, and the saving method deciding unit 1341 decides an image format for saving data, based on the image features. Specific saving method deciding processing will be described in S711 to S721.

Although image features are acquired in S530 in the present embodiment, the step in which image features are acquired is not restricted to this step. For example, an arrangement where image features are acquired immediately after image acquisition in S510 and an arrangement where image features are acquired in S520 are also included in the present invention.

Next, the processing executed in S530 will be described in detail with reference to the flowchart in FIG. 7B.

Step S711: Image Feature Acquisition

The image feature acquiring unit 1342 detects the retinal blood vessel regions and arteriovenous crossing portions as image features from the wide-angle images Dln. The images from which image features are acquired are not restricted to wide-angle images, and cases of deciding the data saving method for image features directly acquired from high-magnification images Dnk, for example, are also included in the present invention. Retinal blood vessels have linear shapes, so the present embodiment employs a retinal blood vessel region detection method where a filter that enhances linear structures is used to extract the retinal blood vessels. Specifically, a wide-angle image Dln is smoothed by a Gaussian function of a size a equivalent to the radius of the arcade blood vessel, and thereupon a tube enhancement filter based on a Hessian matrix is applied, and binarization is performed at a threshold value Ta, thus extracting the arcade blood vessels.

As for the method for detecting arteriovenous crossing portions in the present embodiment, a crossing detection filter disclosed in Japanese Patent Laid-Open No. 2001-070247 is used. Specifically, a crossing portion is determined when there are four or more blood vessel regions at the perimeter of the filter, and there is a blood vessel region at the center portion of the filter. Retinal arteries contain more hemoglobin than retinal veins and thus are higher in luminance, so the lowest luminance value within each of the crossing blood vessel regions is calculated from the detected crossing portions, and in a case where the absolute value among the lowest luminance values is equal to or larger than a threshold value T1, this is determined to be an arteriovenous crossing. Note however, that the crossing detection method is not restricted to this, and any known crossing detection method may be used.

Although description has been made in the present embodiment that the image feature acquiring unit 1342 acquires anatomical features such as arteriovenous crossing portions, the present invention is not restricted to this. For example, a disorder candidate region such as the photoreceptor defect portion Dc5 in FIG. 6K may be acquired as an image feature. Although any detection method of the photoreceptor defect region may be used, detection is made in the present embodiment according to the following procedures. That is to say, each region that has a pixel value smaller than a threshold T2 in an image regarding which Fourier transform is performed in the confocal images Dcj, a low-pass filter is applied to cut out high-frequency signal values, following which inverse Fourier transform is performed, is detected as a photoreceptor defect region.

Step S721: Deciding Image Format for Saving

The saving method deciding unit 1341 decides image types of imaged images to be saved, the image format for saving, based on the image features that the image feature acquiring unit 1342 has acquired in step S711. In retinal vein occlusion, which is a common eye disorder, arteriovenous crossing portions are an area of predilection (blockage of retinal veins), so in the present embodiment, images including arteriovenous crossing portions are allocated large data amounts for saving. Specifically, the determining unit 1343 determines the image type for saving an image including a retinal blood vessel area to be an R channel image Dnr and L channel image Dnl and (R+L) image Dnr+l. The saving method deciding unit 1341 further decides the saving format for all images including an arteriovenous crossing portion to be a 16-bit non-compressed moving image. For images not including an arteriovenous crossing portion, the determining unit 1343 decides to save only (R+L) images Dnr+l, to reduce the data amount, and the saving method deciding unit 1341 decides the image format to be a 16-bit non-compressed moving image. Note whoever, that the type of image to be saved and the image format are not restrictive, and any saving method may be specified.

For example, images Dnr, Dnl, and Dnr+l that include an arteriovenous crossing portion may be decided to be 16-bit non-compressed (R+L) moving images Dnr+l, and other images to be 16-bit non-compressed (R+L) composited images Dnr+l. Alternatively, all image types saved in the determining unit 1343 may be determined to be Dnr and Dnl, and thereupon the saving method deciding unit 1341 decide that images Dnr and Dnl that include an arteriovenous crossing portion may be decided to be 16-bit non-compressed moving images, and other images Dnr and Dnl to be 8-bit non-compressed (R+L) composited images Dnr+l. Alternatively, images Dnr, Dnl, and Dnr+l that include an arteriovenous crossing portion may be decided to be non-compressed AVI files, and other images Dnr, Dnl, and Dnr+l to be an AVI file encoded by a predetermined codec (e.g., Motion JPEG).

Note that in a case where a disorder candidate such as a photoreceptor defect region is to be acquired as an image feature in S711, there is the possibility that a region will be included where the photoreceptors are detected only by non-confocal images, so the saving method is decided by the following procedures. That is to say, Is=(number of photoreceptor positions detected from only one of confocal images Dcj and non-confocal image Dnk)/((number of positions where photoreceptor have been detected from both image types)+(number of photoreceptor positions detected from only one of confocal images Dcj and non-confocal image Dnk)). Assumption is made here that Split Detector images are being generated as non-confocal images Dnk.

It is generally understood that photoreceptors, which are an example of observation, become defective from the outer segments, next become defective at the inner segments, and finally reach necrosis. Scoles and Dubra describe that confocal images Dcj enable photoreceptor outer segment defects to be observed, while non-confocal images Dnk enable photoreceptor inner segment defects to be observed. Accordingly, at positions where photoreceptors cannot be visually recognized from confocal image Dc5 illustrated in FIG. 6K and the photoreceptors can be visually recognized from non-confocal image Dn5 in FIG. 6L, the outer segments of the photoreceptors are defective but the inner segments are sound, meaning that this is a crucial image for observation and analysis, since there is a chance for recovery.

Accordingly, in a case where Is is equal to a threshold value T3 or higher, the determining unit 1343 decides Dcj and Dnk to be the objects of saving, and the saving method deciding unit 1341 decides to save Dcj as 16-bit non-compressed moving images and composited images, and to save Dnk as 16-bit non-compressed composited images. In the other hand, in a case of images where Is is smaller than threshold T3, and images where the confocal images Dcj contain no photoreceptor defect regions, the determining unit 1343 decides that these are not crucial images for observation and analysis, and decides only to save the confocal images Dcj, and the saving method deciding unit 1341 decides to save as 16-bit non-compressed composited images. Note that an arrangement may be made where, regardless of the magnitude of Is, just the images of both confocal images Dcj and non-confocal images Dnk are saved in a predetermined format (i.e., composited images), with the images being saved as 16-bit images if Is is threshold T3 or larger and saved as 8-bit images for cases where Is is smaller than T3 and for cases where photoreceptor defect regions are not included. Alternatively, Dcj and Dnk may both be saved as moving images regardless of the magnitude of Is, with the images being saved as non-compressed AVI if Is is threshold T3 or larger and saved as AVI files encoded by a predetermined codec for cases where Is is smaller than T3 and for cases where photoreceptor defect regions are not included. Any known compression method and image format may be used as the compression method and image format according to the present invention.

According to the above-described configuration, when taking images by an SLO apparatus to acquire confocal images and non-confocal images, the information processing apparatus 10 allocates more data amount for saving, the more crucial portions for observation and image analysis the image includes, based on image features and disorder candidate regions acquired in the images. Accordingly, eye images that are crucial for observation and analysis can be efficiently saved.

Third Embodiment: Deciding Image Saving Method by Image Analysis Results

Figure 9:
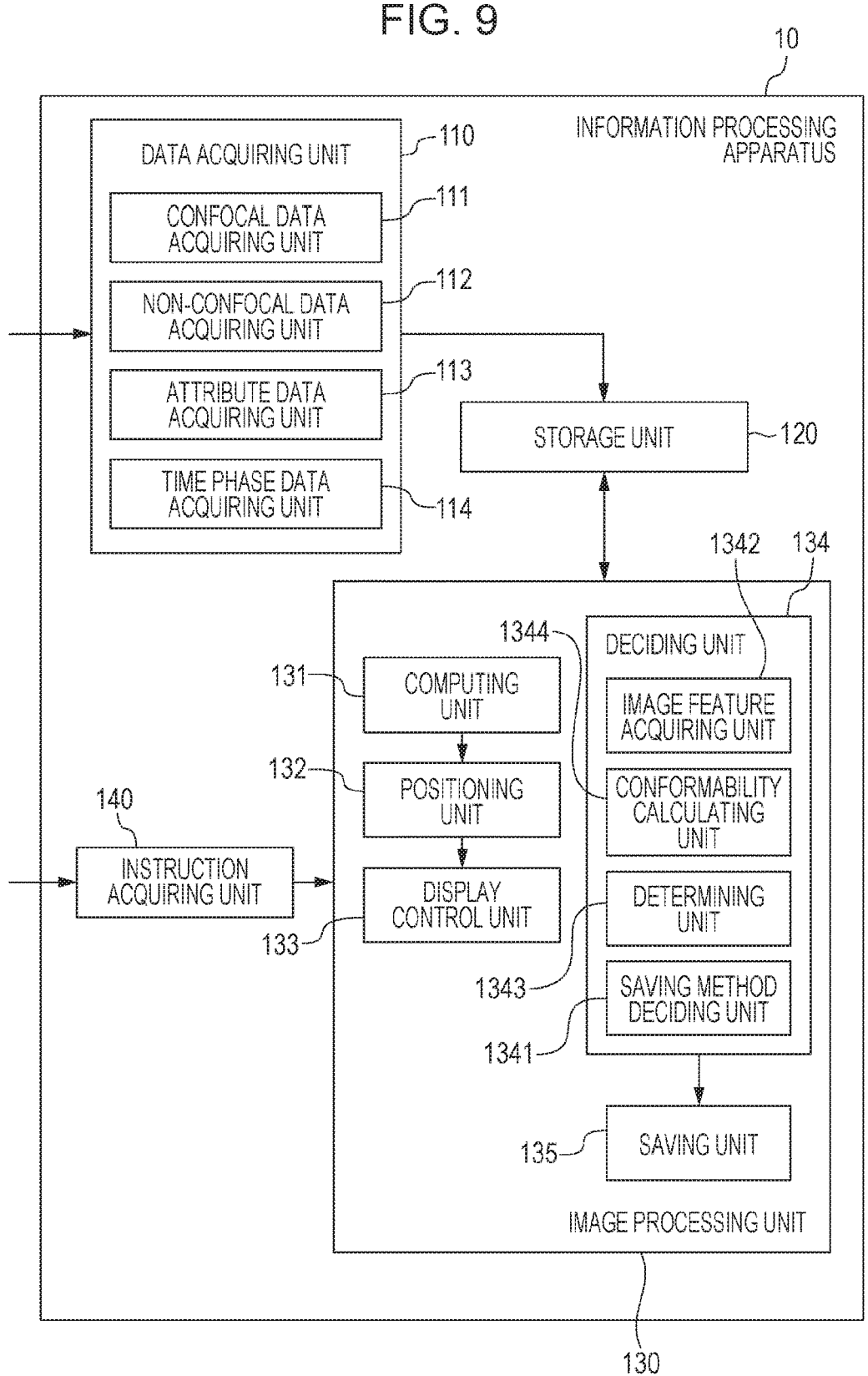
FIG. 9 is a block diagram illustrating a functional configuration example of an information processing apparatus according to a third embodiment.
Figure 10:
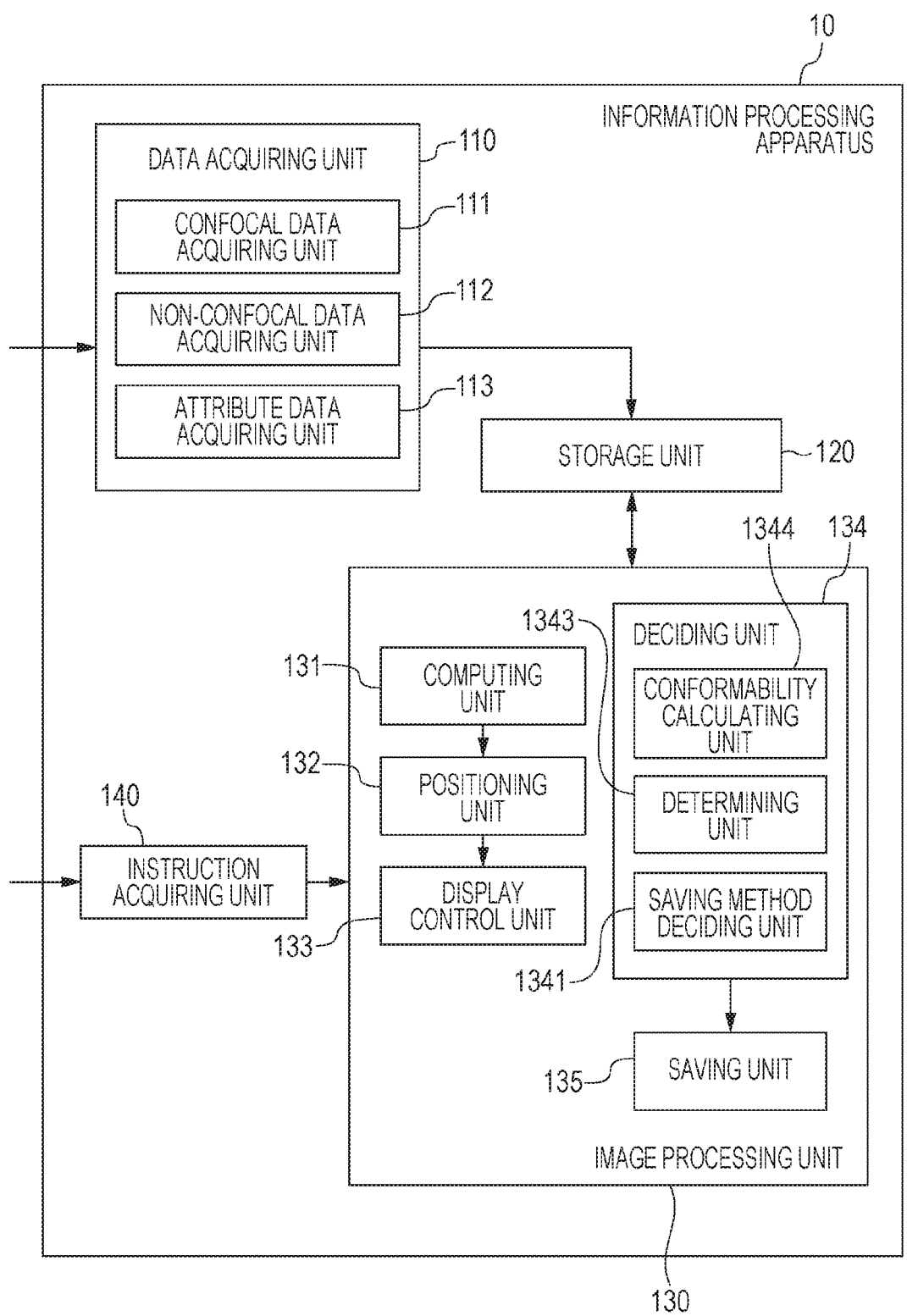
FIG. 10 is a block diagram illustrating a functional configuration example of an information processing apparatus according to a fourth embodiment.

An information processing apparatus according to a third embodiment is configured to decide an image saving method based on not only image attributes or image features (disorder candidates) acquired from the image, but also analysis results from analyzing the image, which is to say image quality, and percentage of an imaging object region in an image. Specifically, description will be made regarding a data saving method, decided based on image analysis results, in a case where the same retinal blood vessels are taken as confocal images Dcj and two types of non-confocal images Dnk (non-confocal images taken with the aperture opened to a large diameter and moved to the right side and left side along the retinal blood vessels). The configuration of apparatuses connected to the information processing apparatus 10 according to the present embodiment is the same as in the case in the second embodiment. FIG. 9 is a functional block diagram of the information processing apparatus 10 according to the present embodiment. This differs from the arrangement in the second embodiment with regard to the point that the deciding unit 134 includes a conformability calculating unit 1344. The image processing flow according to the present embodiment is the same as in FIG. 5, and is the same as the second embodiment except for S530. Accordingly, only S530 will be described in the present embodiment. Hereinafter, of the two types of non-confocal images, images acquired by moving the aperture to the right side of the retinal blood vessels will be denoted by Dnr, and images acquired by moving the aperture to the left side of the retinal blood vessels will be denoted by Dnl. These images are acquired with the aperture (pinhole) opened wide.

Step S530: Deciding Data Saving Method

The image feature acquiring unit 1342 acquires the retinal blood vessel regions and arteriovenous crossing portions as image features from the wide-angle images Dln. Further, the conformability calculating unit 1344 calculates the conformability based on the image quality of acquired image, and the percentage that the region actually imaged occupies in the region to be imaged, and the saving method deciding unit 1341 decides the image format for saving data, based on the image features and conformability. Note that an arrangement may be made where the attribute data acquiring unit 113 acquires the attribute data rather than the image feature acquiring unit 1342 acquiring image features in this step. Specific saving method deciding processing will be described in detail in S712, S722, and S732.

Next, the processing executed in S530 will be described in detail with reference to the flowchart illustrated in FIG. 7C.

Step S712: Acquiring Attribute Information or Image Features

The image feature acquiring unit 1342 acquires retinal blood vessel regions and arteriovenous crossing portions as image features from the wide-angle images Dln. The method of acquiring the retinal blood vessel regions and arteriovenous crossing portions is the same as in the second embodiment, so description will be omitted. Cases where the image feature acquiring unit 1342 acquires disorder candidates such as photoreceptor defect in step S711 in the second embodiment are also included in the present invention. The specific method of acquiring photoreceptor defect region is the same as in the second embodiment, so description will be omitted. Also, an arrangement may be made in the present invention where the attribute data is acquired instead of acquiring image features. That is to say, the attribute data acquiring unit 113 acquires attribute data relating to each image. Examples of attribute data that is acquired include image type (confocal image/R channel image/L channel image), resolution, number of gradations, and number of frames.

Step S722: Calculating Image Conformability

The conformability calculating unit 1344 calculates the conformability based on the image quality of each image, and the percentage of the region actually imaged occupies in the region to be imaged. For image quality, the signal-to-noise (S/N) ratio is calculated. The index of the image quality is not restricted to this, and any known image quality index may be used. For example, Contrast-Noise Ratio (CNR) may be calculated. Also, a value indicating whether the region to be imaged has been sufficiently imaged is calculated by (area of region imaged in all frames)/(area of region to be imaged). In the present embodiment, conformability is expressed as $\omega 1 \cdot Iq + \omega 2 \cdot Ic$, where Iq is 1 if the S/N ratio is equal to or larger than a threshold T4, and is 0 if the S/N ratio is smaller than threshold T4. Ic is (area of region imaged in all frames)/(area of region to be imaged). $\omega 1$ and $\omega 2$ are weighting parameters that can be specified optional values in the range of 0 to 1. Both are 0.5 in the present embodiment.

Step S732: Deciding Image Format for Saving

The saving method deciding unit 1341 decides the image format for saving data, based on the image features acquired by the image feature acquiring unit 1342 and the conformability calculated by the conformability calculating unit 1344. In the present embodiment, the determining unit 1343 determines R channel images Dnr and L channel images Dnl that have conformability equal to or above a threshold T5, to be the object of saving. The saving method deciding unit 1341 decides regarding images Dnr and Dnl, in the images that are the object of saving, including arteriovenous crossing portions, to save moving images and composited images, and regarding images Dnr and Dnl not including arteriovenous crossing portions, to save composited images. Further, images Dnr and Dnl including arteriovenous crossing portions and having conformability equal to or above a threshold T6 (where T5<T6) are decided to be saved as uncompressed AVI files, while images having conformability smaller than threshold T6 are decided to be saved as AVI files encoded by a predetermined codec. Although an image format for saving data has been described as being decided in the present embodiment based on image features and conformability, the present invention is not restricted to this. For example, the image format for saving data may be decided based on attribute data acquired in S712 and conformability.

While the conformability has been described as being calculated by the conformability calculating unit 1344 based on the image quality and the percentage including the region to be imaged, the calculating method of conformability is not restricted to this, and any calculating method may be used as long as based on coordinates and pixel values of the imaged images. For example, the conformability may be calculated based on luminance characteristics of the imaged images, i.e., luminance values and statistics relating to the luminance values. Specifically, the average luminance value of the image that has been imaged may be calculated, and a value where this average luminance value is weighted may be used as the conformability. Alternatively, the contrast of the imaged images (maximum luminance−minimum luminance)/(maximum luminance+minimum luminance) may be calculated as conformability.

According to the configuration described above, the information processing apparatus 10 decides generating methods and measuring methods for image using not only image attributes or image features (disorder candidates) acquired from the images, but also using image acquisition results, i.e., image quality and percentage including region to be imaged. Thus, images of the eye that are crucial for observation and measurement can be efficiently generated or measured.

Fourth Embodiment: Deciding Image Saving Method Based on Processing Results by Examination Date The information processing apparatus 10 according to the present embodiment is configured such that, based on image attributes acquired on different examination dates, the more examination dates on which saving has been performed there are in attributes of an image, the more data amount is allocated for saving. Specifically, in a case where confocal images and non-confocal images including a photoreceptor outer segment defect region have been acquired on different examination dates, the following processing is performed. That is to say, description will be made regarding a case where the attributes of these image groups taken on different examination dates are acquired, the more examination dates of saving there are in attributes of an image, the more data amount is allocated for saving of that image. The configuration of apparatuses connected to the information processing apparatus 10 according to the present embodiment is the same as in the first embodiment. The configuration of apparatuses connected to the information processing apparatus 10 according to the present embodiment differs from that in the third embodiment with regard to the points that the data acquiring unit 110 does acquires examination data of different examination dates, the deciding unit 134 does not have the image feature acquiring unit 1342, and the conformability calculating unit 1344 calculates conformability as to past examination images based on the attributes of images on different examination dates.

The information processing flow according to the present embodiment is illustrated in FIG. 5, and is the same as the third embodiment except for S510, S520, and S530. Accordingly, S510, S520, and S530 will be described in the present embodiment. Confocal images and non-confocal images in past examinations are denoted by Dcjf and Dnkf (where f=1, 2, . . . , e−1, f being a natural number indicating the No. of the examination in serial order). Confocal images and non-confocal images in the current examinations are denoted by Dcje and Dnke.

Step S510: Acquiring Images

Next, the data acquiring unit 110 requests the SLO imaging apparatus 20 for acquisition of wide-angle images Dlce and Dlne, confocal images Dcje and non-confocal images Dnke, and fixation target positions Fle and Fcne corresponding to the current examination. In the present embodiment, the wide-angle images Dlce and Dlne, confocal images Dcje, and non-confocal images Dnke are acquired with fixation target positions Fle at the fovea and fixation target positions Fcne at the fovea and parafovea. Note that the imaging position setting method is not restricted to this, and the imaging position may be set to an optional position. The SLO imaging apparatus 20 acquires and transmits the wide-angle images Dlce and Dlne, confocal images Dcje and non-confocal images Dnke, and fixation target positions Fle and Fcne, in response to the acquisition request. The data acquiring unit 110 receives the wide-angle images Dlce and Dlne, confocal images Dcje, non-confocal images Dnke, and fixation target positions Fle and Fcne, from the SLO imaging apparatus 20 via the LAN 30. The data acquiring unit 110 stores the received wide-angle images Dlce and Dlne, confocal images Dcje, non-confocal images Dnke, and fixation target positions Fle and Fcne in the storage unit 120.

Step 520: Display

The non-confocal data acquiring unit 112 additionally generates Split Detector images Dlns and Dnsk as nonconfocal images, and stores in the storage unit 120. Next, the positioning unit 132 performs inter-frame positioning and image tiling processing on the wide-angle images Dlce and Dlne and confocal images Dcje and Dnke of the current inspection. Specific processing procedures are the same as in S520 in the first embodiment, so description will be omitted. The display control unit 133 displays the image group formed so far on the monitor 305. The composited images here are displayed tiled using the positioning parameter values. Composited image or inter-frame positioned moving images are displayed using the inter-frame positioning parameters are displayed regarding a imaging position instructed via the instruction acquiring unit 140.

Step 530: Deciding Data Saving Method

The attribute data acquiring unit 113 acquires attribute data relating to all examination images. Further, the conformability calculating unit 1344 calculates the conformability of the images from the current examination as to the past examination images, based on the attribute information of the past examination images, and thereupon the saving method deciding unit 1341 decides an image format for saving data, based the conformability. Specifics of deciding the saving method will be described in detail in S713, S723, and S733.

Next, processing executed in S530 will be described in detail with reference to the flowchart illustrated in FIG. 7D.

Step S713: Acquiring Attribute Information for all Examination Images

The attribute data acquiring unit 113 acquires attribute data relating to all examination images. In the present embodiment, the image type of each image (confocal images/R channel images/L channel images/Split Detector images), resolution, number of gradients, number of frames, and data compression format is acquired as attribute data.

Step S723: Calculate Conformability of Image

The conformability calculating unit 1344 calculates the conformability of the images of the current examination as to past corresponding examination images, based on the attribute information of the past examination images. In the present embodiment, the conformability Irn as to past examination images is calculated by Irn=(gross number of images in all examinations having the same acquisition position, focal position, and image type, that were actually saved)/(total number of examinations).

Step S733: Deciding Image Format for Saving

The saving method deciding unit 1341 decides the image format for saving data, based on the conformability as to past corresponding examination images, calculated in S723. The determining unit 1343 determines images having conformability calculated in S723 equal to or above a threshold T7 to be the objects of saving confocal images Dcj and Split Detector images Dnk, and images smaller than threshold T7 to be the objects of saving only confocal images Dcj. The saving method deciding unit 1341 also decides to save the former as moving images and composited images, and the latter as composited images. Further, the saving method deciding unit 1341 decides to allocate more data amount for saving images which have been saved on more examination dates, based on the conformability calculated in S723. Images of which the conformability calculated in S723 is smaller than a threshold T8 are decided to be saved by 8-bit lossless compression, resolution of half the original image, and the same number of frames as the original image. Images of which the conformability is threshold T8 or above but smaller than a threshold T9 are decided to be saved by 16-bit lossless compression, and the same resolution and the same number of frames as the original image. Images of which the conformability is threshold T9 or above are decided to be saved by 16-bit non-compressed, and the same resolution and the same number of frames as the original image. Note that the image formats for saving that are decided based on the calculated conformability are not restricted to these, and any image format may be decided.

According to the information processing apparatus 10 configured as described above, based on image attributes acquired on different examination dates, the more examination dates of having been saved there are in attributes of an image, the more data amount is allocated to that image. Accordingly, in a case of comparing and observing images of different examination dates, eye images that are crucial for observation and analysis can be efficiently saved.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-093538, filed Apr. 30, 2015, which is hereby incorporated by reference herein in its entirety.

What is claimed is:

1. An information processing apparatus comprising:
   an image acquiring unit configured to acquire a plurality of types of images of an eye, including a confocal image and a non-confocal image of the eye;
   a deciding unit configured to independently decide a saving format for saving the confocal image and non-confocal image in a storage region so that the relation in magnitude of at least one of the number of frames and the amount of data differs between the confocal image saved in the storage region and the non-confocal image saved in the storage region; and
   a saving unit configured to save at least one of the acquired plurality of types of images in the storage region, based on the decided saving format.

2. The information processing apparatus according to claim 1,
   wherein the deciding unit decides the saving format for saving the confocal image and non-confocal image in the storage region, based on an object of observation in the acquired plurality of images, the object of observation being one of objects of observation corresponding to different focusing positions of the eye.

3. The information processing apparatus according to claim 1,
wherein the deciding unit decides the saving format so that the relation in magnitude differs between the number of frames of the confocal image saved in the storage region and the number of frames of the non-confocal image saved in the storage region, based on an object of observation in the acquired plurality of images, the object of observation being one of objects of observation corresponding to different focusing positions of the eye.

4. The information processing apparatus according to claim 3,
wherein, in a case where the object of observation is photoreceptors, the deciding unit decides the saving format so that the number of frames of the confocal image saved in the storage region is larger than the number of frames of the non-confocal image saved in the storage region, and in a case where the object of observation is blood vessels, the decides the saving format so that the number of frames of the confocal image saved in the storage region is smaller than the number of frames of the non-confocal image saved in the storage region.

5. The information processing apparatus according to claim 1,
wherein the deciding unit decides the saving format so that the relation in magnitude differs between the amount of data of the confocal image saved in the storage region and the amount of data of the non-confocal image saved in the storage region, based on an object of observation in the acquired plurality of images, the object of observation being one of objects of observation corresponding to different focusing positions of the eye.

6. The information processing apparatus according to claim 5,
wherein, in a case where the object of observation is photoreceptors, the deciding unit decides the saving format so that the amount of data of the confocal image saved in the storage region is larger than the amount of data of the non-confocal image saved in the storage region, and in a case where the object of observation is blood vessels, the decides the saving format so that the amount of data of the confocal image saved in the storage region is smaller than the amount of data of the non-confocal image saved in the storage region.

7. The information processing apparatus according to claim 1, further comprising:
a specification unit configured to specify different saving formats for each type of image in the acquired plurality of image types,
wherein the deciding unit decides the specified saving format.

8. The information processing apparatus according to claim 7,
wherein the specification unit specifies whether or not to save the acquired plurality of types of images in the storage region.

9. The information processing apparatus according to claim 1,
wherein the information processing apparatus is communicably connected to an ophthalmologic imaging apparatus that a plurality of types of images of the eye,
and wherein the image acquiring unit acquires a plurality of types of images obtained by imaging the eye at generally the same time.

10. The information processing apparatus according to claim 9,
wherein the ophthalmologic imaging apparatus includes
a shared light source to acquire a confocal image and a non-confocal image of the eye, and
an optical member that splits returning light from the eye irradiated by light from the light source, into returning light passing through a confocal region and returning light passing through a non-confocal region,
and wherein the image acquiring unit acquires the confocal image based on the returning light passing through the confocal region, and acquires the non-confocal image based on the returning light passing through the non-confocal region.

11. The information processing apparatus according to claim 10,
wherein the image acquiring unit acquires the confocal image and non-confocal image of the eye, obtained by adjusting at least one of a position and a shape of an aperture disposed upstream of a light-receiving portion that receives light of at least one of returning light passing through the confocal region and returning light passing through the non-confocal region.

12. The information processing apparatus according to claim 10,
wherein an acquisition position of the confocal image and an acquisition position of the non-confocal image of the eye are the same.

13. An operation method of an information processing apparatus, the method comprising:
a step of acquiring a plurality of types of images of an eye, including a confocal image and a non-confocal image of the eye;
a step of deciding independently a saving format for saving the confocal image and non-confocal image in a storage region so that the relation in magnitude of at least one of the number of frames and the amount of data differs between the confocal image saved in the storage region and the non-confocal image saved in the storage region; and
a step of saving at least one of the acquired plurality of types of images in the storage region, based on the decided saving format.

14. A non-transitory computer-readable storage medium storing a program for causing a computer to execute the method according to claim 13.

15. The information processing apparatus according to claim 1,
wherein the deciding unit decides the saving format based on an object of observation in the acquired plurality of images.

16. The information processing apparatus according to claim 15,
wherein, in a case where the object of observation is photoreceptors, the deciding unit decides the saving format so that the number of frames of the confocal image saved in the storage region is larger than the number of frames of the non-confocal image saved in the storage region, and in a case where the object of observation is blood vessels, the decides the saving format so that the number of frames of the confocal image saved in the storage region is smaller than the number of frames of the non-confocal image saved in the storage region.

17. The information processing apparatus according to claim 15,
wherein, in a case where the object of observation is photoreceptors, the deciding unit decides the saving format so that the amount of data of the confocal image saved in the storage region is larger than the amount of data of the non-confocal image saved in the storage region, and in a case where the object of observation is blood vessels, the decides the saving format so that the amount of data of the confocal image saved in the storage region is smaller than the amount of data of the non-confocal image saved in the storage region.

* * * * *